United States Patent [19]
Phillips

[11] Patent Number: 5,593,388
[45] Date of Patent: Jan. 14, 1997

[54] INJECTOR WITH RETRACTABLE SHROUD

[75] Inventor: Ian R. Phillips, Killara, Australia

[73] Assignee: N.J. Phillips Pty. Limited, New South Wales, Australia

[21] Appl. No.: 339,392

[22] Filed: Nov. 14, 1994

[30] Foreign Application Priority Data

Nov. 11, 1993 [AU] Australia ................. PM2350

[51] Int. Cl.⁶ ........................................ A61M 5/20
[52] U.S. Cl. ............................. 604/135; 604/131
[58] Field of Search ..................... 604/134, 135, 604/136, 137, 181, 192, 198, 263

[56] References Cited

U.S. PATENT DOCUMENTS

| | | | |
|---|---|---|---|
| 2,752,918 | 7/1956 | Uytenbogaart | 604/136 |
| 3,430,626 | 3/1969 | Bergman | 604/137 |
| 3,494,358 | 2/1970 | Fehlis et al. | 604/137 |
| 4,403,989 | 9/1983 | Christensen et al. | 604/137 |
| 4,530,695 | 7/1985 | Phillips et al. | 604/134 X |
| 4,642,009 | 2/1987 | Phillips et al. | 604/136 |
| 4,676,781 | 6/1987 | Phillips et al. | 604/136 X |
| 4,717,383 | 1/1988 | Phillips et al. | 604/135 |

FOREIGN PATENT DOCUMENTS 2620358  11/1977  Germany ................. 604/137

*Primary Examiner*—Sam Rimell
*Attorney, Agent, or Firm*—Ladas & Parry

[57] ABSTRACT

An injector (10) having a needle (14) which is exposed by a retractable shroud (13). Mounted within the body (11) of the injector (10), is a first interacting piston (30) and cylinder (31) which cooperate to enclose a first space (33) which receives the liquid to be injected. A second interacting piston (26) and cylinder (27) cooperate to enclose a second space (28). A gas under pressure is delivered to the second space (28) to cause movement of the second piston (26). The second piston (26) is attached to the first piston (30) and therefore moves with it. The shroud (13) is operatively associated with a valve (35) to regulate the delivery of the gas under pressure to the space (28) to cause operation of the injector (10). A user of the injector (10) grips the body (11) by means of a handle portion (12) and presses the injector (10) against the skin of the animal. This causes retraction of the shroud (13) as the needle (14) penetrates. That retraction of the shroud (13) then causes actuation of the valve (35) to cause operation of the injector (10).

11 Claims, 2 Drawing Sheets

INJECTOR WITH RETRACTABLE SHROUD

TECHNICAL FIELD

The present invention relates to injectors to deliver medication to animals. More particularly, the present invention relates to injectors which are powered by a pressurised gas.

BACKGROUND OF THE INVENTION

Injectors with a needle are used to deliver medication directly to animals. As one example, injectors are used to deliver medication directly to the rumen of an animal.

Disclosed in U.S. Pat. No. 4,530,695 is an injector having a needle enabling a medication to be directly delivered via the needle. The injector has an interacting piston and cylinder. The injector is "cocked" by a user tensioning a spring. The forward portion of the injector is provided with a trigger mechanism which when activated releases the cylinder which moves over the piston to cause the medication to be injected via the needle. The user then recocks the device. The trigger is operated by the forward portion of the injector contacting the skin of the animal. This injector in its preferred construction was adapted as an intraruminal injection apparatus. Another intraruminal injector is disclosed in U.S. Pat. No. 4,403,989. In this device, an interacting piston and cylinder are moved by the operator to cause injection to take place. A trigger mechanism releases the piston and cylinder for this relative movement. Again it is the the operator which provides the force required to operate the device. A multi dose injector is described in U.S. Pat. No. 2,821,193. In this device, a pump mechanism is employed to operate the device. The pump mechanism is trigger operated requiring the operator to reciprocate the trigger to operate the pump mechanism. Again it is the operator which provides the force to operate the device. A further multi-dose injector is described in U.S. Pat. No. 3,400,716. This device requires the operator to push the device against the skin in order to operate the piston and cylinder assembly. Again the user requires the force to operate the device.

Disclosed in U.S. Pat. No. 4,676,781 is a still further ruminal injector. This device has an interacting piston and cylinder but no trigger mechanism. The device is operated by the user pushing the device against the animal. Again the user provides the force required to operate the device. European Patent Publication 0080112 also discloses an injector. The injector is provided with a reservoir with a trigger mechanism which pumps the vaccine from the reservoir to the needle. Again the operator provides the force required to operate the device.

A still further injector is described in German Patent Specification 1,491,840. This device uses an interacting piston and cylinder and a spring mechanism which is cocked prior to use. Again the user provides the force required to operate the device.

In each of the above described devices, it is the user that provides the force required to operate the device.

OBJECT OF THE INVENTION

It is the object of the present invention to overcome or substantially ameliorate the above disadvantages.

SUMMARY OF THE INVENTION

There is disclosed herein an injector comprising:
a body having a forward end;
a needle extending away from said forward end;
a first interacting piston and cylinder mounted in said body and cooperating to enclose a first variable volume space;
a second interacting piston and cylinder mounted in said body and cooperating to enclose a second variable volume space;
a first passage extending from said first space to said needle so that upon a reduction in the volume of said first space, a liquid contained therein is caused to move from said first space through said first passage to said needle wherefrom the liquid is injected;
a second passage extending from said second space to enable a fluid under pressure to be delivered thereto to cause relative movement between said second piston and cylinder;
a connection between said first piston and cylinder and said second piston and cylinder so that said relative movement between said first and second cylinders to reduce the volume of said first space;
a valve connected to said second passage to regulate the supply of said fluid to said second space;
a delivery duct extending to said first space to permit the liquid to be injected to be delivered thereto;
a trigger member extending away from said forward end, said trigger member being movable in the direction of extension of the needle between an extended position and a retracted position, said trigger member being mounted relative to said needle so that upon penetration of said needle said trigger member is moved from said extended position towards said retracted position; and wherein
said trigger member is operatively associated with said valve to cause operation thereof to deliver said fluid to said second space upon said trigger member moving a predetermined distance from said extended position towards said retracted position.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENT

Figure 1:
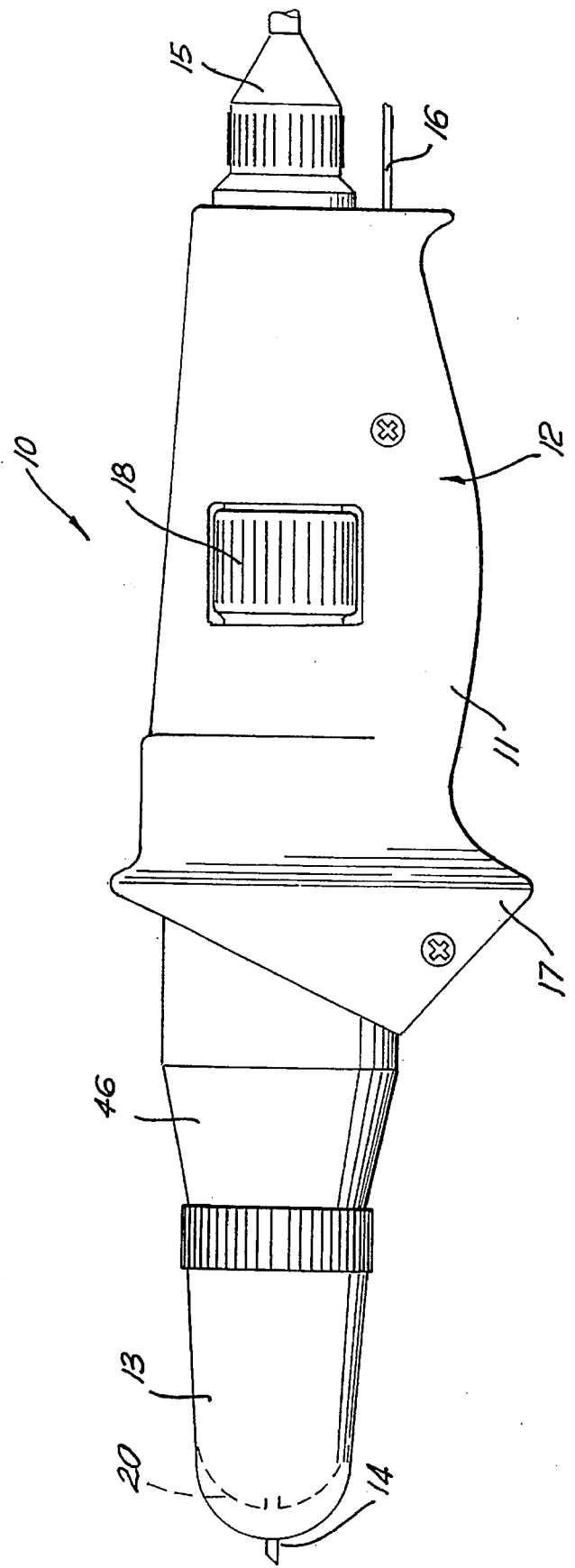
FIG. 1 is a schematic side elevation of an injector.
Figure 2:
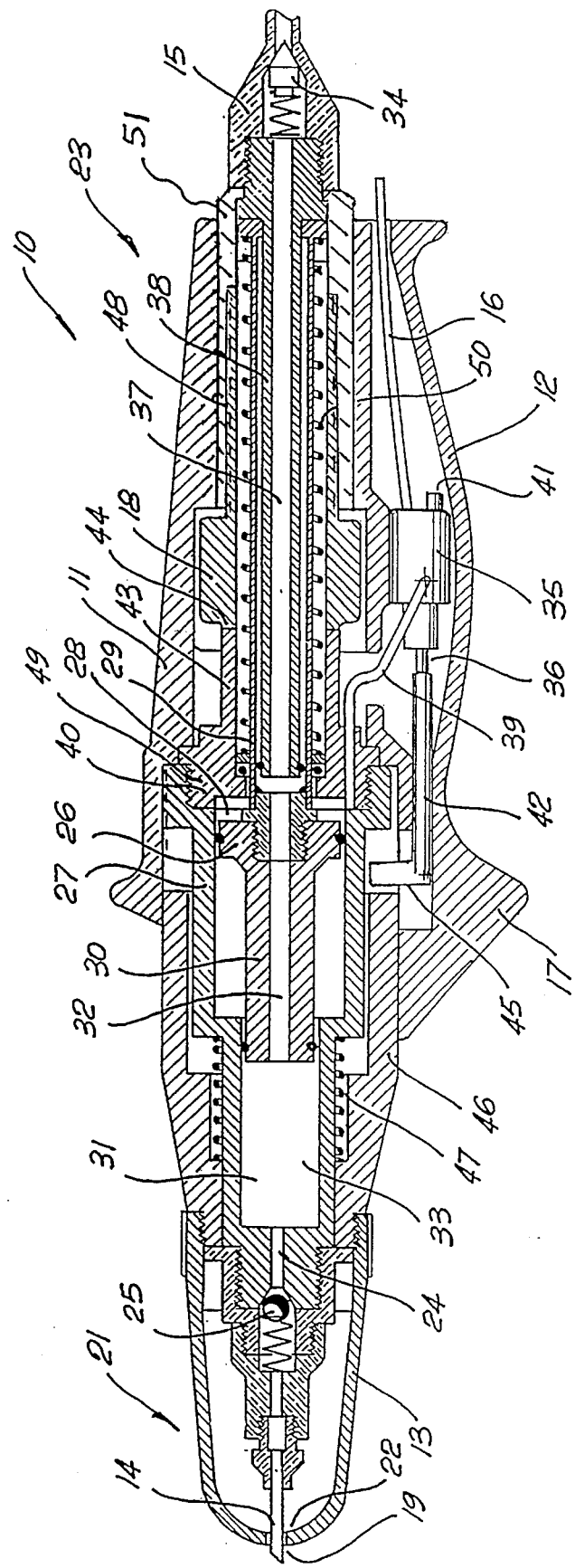
FIG. 2 is a schematic sectioned side elevation of the injector of FIG. 1.

In the accompanying drawings there is schematically depicted an injector 10 comprising a body 11 having a handle portion 12. The body 11 has a forward end 21 from which there extends a needle 14. Movably mounted in front of the forward end 21 is a retractable shroud 13 which is movable between an extended position covering the needle tip 19 and a retracted position 20 exposing a substantial portion of the needle 14. The shroud 13 is retracted by contact with the skin of the animal. As the needle 14 penetrates the animal, the shroud 13 is pushed towards the rear portion 23 of the body 11. The shroud 13 has an opening 22 through which the tip 19 passes. The shroud 13 provides a trigger member for the injector 10.

Located within the body 11 is a first interacting piston 30 and cylinder 31, which cooperate to enclose a variable volume first space 33. Extending from the space 33 is a first passage 24 which communicates with the needle 14 via a one-way valve assembly 25. The one-way valve assembly 25 permits liquid to flow only in the direction from the space 33 to the needle 14. The needle 14 is mounted in the forward end of the cylinder 31, as is the shroud 13.

A second cooperating piston 26 and cylinder 27 cooperate to enclose a variable volume second space 28. Extending from the piston 26 is the piston 30 so that upon enlargement of the space 28, there is a corresponding decrease in the volume of the space 33. The space 28 is closed by a rear closure member 40 through which there extends a duct member 29, also attached to the piston 26. The duct member 29 has a central passage 37 through which the medication to be injected passes to enter the space 33 by means of a bore 32 extending through the piston 30 and communicating with the passage 37. Slidably located within the passage 37 and sealingly engaged in the internal surface of the duct member 29 is a sleeve 38. The sleeve 38 is fixed to the inlet port 15, which is attached to a reservoir containing the medication to be injected. The inlet port 15 contains a one-way valve 34 which restricts the medication to move in the direction towards the space 33. Sealing sliding movement between the duct member 29 and sleeve 38 permits relative movement between the piston 26 and the body 11 while still permitting the medication to be delivered to the space 33.

Communicating with the space 28 is trigger operated valve 35 via a conduit 39. The trigger operated valve 35 is connected to a supply of fluid, preferably a gas under pressure via a further conduit 16 providing an inlet for the gas under pressure. In this regard it should be appreciated that other fluids, such as liquids, could be used as a driving medium. The trigger valve 35 is also provided with an exhaust port 41. The trigger valve 35 is operated by a button 36 which either connects the conduit 39 to the conduit 16 or the exhaust port 41. The button 36 in its extended position would operatively connect the conduit 39 to the exhaust port 41 permitting gas to exit from the space 28. In its depressed position, the button 36 would operate the valve 35 so that the conduit 16 would operatively connected to the conduit 39, thereby delivering gas under pressure to the space 28.

The button 36 is moved by means of a trigger slide 42. The slide 42 has an abutment end 45 which is engaged by a shroud slide 46. The shroud slide 46 is slidably mounted within the body 11 and is attached to the shroud 13.

A spring 47 engages the shroud slide 46 to bias the shroud slide 46 to move the shroud 13 to a position covering the needle 14.

The volume of medication to be injected is adjusted by means of an adjustment wheel 18. The adjustment wheel 18 is rotatably mounted within the body 11 by being threadably engaged therewith via a threaded section 48 the sleeve 51. Rotation of the adjustment wheel 18 about the longitudinal axis of the injector 10 causes relative longitudinal movement of the piston 30 relative to adjustment wheel 18. Adjustment wheel 18 abuts an end portion 44 of a plug 43, with the other end 49 of the plug 43 abutting the piston 30. Accordingly longitudinal movement of the wheel 18 will cause a corresponding longitudinal movement of the cylinder 27. As the cylinders 27 and 31 are integrally formed, the cylinders 27 and 31 move relative to the and pistons 26 and 30, to thereby vary the maximum volume of the space 33, and therefore the volume of the liquid to be injected. The sleeve 51 slides in the body 11 and is fixed to the sleeve 38.

The handle portion 12 has a flared part 17 which enables a user to grip the handle portion 12 and press the injector 10 against the skin of an animal. In doing so, the shroud 13 is retracted and the needle 14 penetrates. Once the shroud 13 has been retracted a predetermined distance and therefore the needle 14 inserted, the valve 35 is triggered by movement of the slide 42 which is engaged by the shroud slide 46. A gas under pressure is then delivered to the second space 28 causing movement of the piston 26 and therefore the piston 30. The volume of the space 33 is reduced and forces the medication out through the needle 14. Upon the return stroke (under the influence of the spring 50) medication is drawn in through the passage 37 and through the bore 32 to be delivered to the space 33.

What I claim is:

1. An injector comprising:

a body having a forward end;

a needle extending away from said forward end and through which a volume of liquid is to be injected;

a first interacting piston and cylinder mounted in said body and cooperating to enclose a first variable volume space;

a second interacting piston and cylinder mounted in said body and cooperating to enclose a second variable volume space;

a first passage extending from said first space to said needle so that upon a reduction in the volume of said first space, liquid contained therein is caused to move from said first space through said first passage to said needle wherefrom the liquid is injected;

a second passage extending from said second space to enable a fluid under pressure to be delivered thereto cause to relative movement between said second piston and cylinder;

a connection between said first piston and cylinder and said second piston and cylinder so that said relative movement causes movement between said first and second cylinders to reduce the volume of said first space;

a valve connected to said second passage to regulate supply of said fluid to said second space;

a delivery duct extending to said first space to permit the liquid to be injected to be delivered thereto;

a trigger member extending away from said forward end, said trigger member being movable in a direction generally parallel to the needle between an extended position and a retracted position, said trigger member being mounted relative to said needle so that upon penetration of said needle said trigger member is moved from said extended position towards said retracted position; and wherein said trigger member is operatively associated with said valve to cause operation thereof to deliver said fluid to said second space upon said trigger member moving a predetermined distance from said extended position towards said retracted position.

2. The injector of claim 1, further including a valve in said first passage restricting liquid in said first passage to flow from said first space to said needle, a valve in said delivery duct restricting liquid to flow towards said first space, and a first spring operatively associated with said first and second pistons to cause relative movement therebetween to maximize the volume of said first space.

3. The injector of claim 2, wherein said spring acts to cause movement of said second piston to thereby cause movement of said first piston.

4. The injector of claim 3 further including a second spring, said second spring being operatively associated with said trigger member to cause movement thereof to said extended position.

5. The injector of claim 4, wherein said second cylinder is an extension of said first cylinder, and said first piston is an extension of said second piston.

6. The injector of claim 5, wherein the cylinders are mounted in the body for movement between a first position at which said first space has a maximum volume, and a second portion at which said first space has a minimum volume, and wherein said injector further includes a volume adjustor for said first space, which adjustor determines said maximum volume to thereby permit adjustment of the volume of said liquid to be injected, and said needle is fixed to said first cylinder and said trigger member is movably mounted on said first cylinder.

7. The injector of claim 6, wherein said adjustor is a movable adjustment member operatively extending between said body and the pistons to cause movement of the pistons relative to the body and relative to the cylinders to thereby change the maximum volume of said space.

8. The injector of claim 7, wherein said adjustment member threadably engages a sleeve so that rotation of said adjustment member causes longitudinal movement of said sleeve to thereby cause movement of the pistons.

9. The injector of claim 7, further including a duct member extending from said pistons, which duct member includes said delivery duct, with said pistons including a bore communicating with said delivery duct to deliver said liquid to said first space.

10. The injector of claim 1, wherein said trigger member is a shroud having an aperture, with said shroud covering said needle when in said extended position, and exposes said needle when in said retracted position, by said needle extending through said aperture.

11. The injector of claim 9, further including a sleeve member slidably located within said duct member so that said duct member slides thereover during movement of the pistons.

\* \* \* \* \*

UNITED STATES PATENT AND TRADEMARK OFFICE
CERTIFICATE OF CORRECTION

PATENT NO. : 5,593,388
DATED : January 14, 1997
INVENTOR(S) : Ian R. Phillips

It is certified that error appears in the above-indentified patent and that said Letters Patent is hereby corrected as shown below:

At column 2, line 19, after "relative" insert -- movement causes--.

At column 2, line 20, "and second cylinders" should be -- piston and cylinder--.

At column 3, line 61, after "18" insert --along sleeve 51--.
At column 3, line 62, "cylinder 27" should be -- port 15--.
At column 4, line 32 (Claim 1, line 17), after "thereto" insert -- to--.

At column 4, line 33 (Claim 1, line 18), delete "to".

At column 4, line 38 (Claim 1, line 23) "second cylinders" should be -- cylinder--.

At column 5, line 8 (Claim 6, line 1) "cylinders" should be -- pistons--.

Signed and Sealed this

Thirteenth Day of May, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,593,388
DATED : January 14, 1997
INVENTOR(S) : Ian R. Phillips

It is certified that error appears in the above-indentified patent and that said Letters Patent is hereby corrected as shown below:

At column 2, line 20, "and second cylinders" should be -- piston and cylinder --.

At column 3, line 61, after "18" insert -- along sleeve 51 --.

At column 3, line 62, "cylinder 27" should be -- port 15 --.

At column 4, line 32 (Claim 1, line 17), after "thereto" insert -- to --.

At column 4, line 33, (Claim 1, line 18), delete "to".

At column 4, line 38, (Claim 1, line 33), "second cyliners" should be -- cylinder --.

At column 5, line 8, (Claim 6, line 1), "cylinders" should be -- pistons --.

Signed and Sealed this

Eleventh Day of November, 1997

Attest:

BRUCE LEHMAN

Attesting Officer

Commissioner of Patents and Trademarks